United States Patent [19]
Jin

[11] Patent Number: 6,124,100
[45] Date of Patent: Sep. 26, 2000

[54] DIAGNOSTIC METHOD AND KIT FOR NEUROPSYCHIATRIC DISEASES USING TRINUCLEOTIDE REPEATS SEQUENCE

[75] Inventor: Dong Kyu Jin, Seoul, Rep. of Korea

[73] Assignee: Samsung Fine Chemicals Co. Ltd., Ulsan, Rep. of Korea

[21] Appl. No.: 09/253,691

[22] Filed: Feb. 22, 1999

[30] Foreign Application Priority Data

Feb. 26, 1998 [KR] Rep. of Korea .......................... 98-6278

[51] Int. Cl.[7] ............................. C12Q 1/68; G01N 19/34; C12N 9/14; C12N 15/00; C07H 21/02; C07H 21/04

[52] U.S. Cl. .......................... 435/6; 435/91.2; 435/320.1; 435/195; 435/810; 536/23.1; 536/24.31; 536/24.33

[58] Field of Search .................. 435/6, 7.9, 91.2, 435/320.1, 401, 810, 195; 536/23.31, 24.33; 436/504

[56] References Cited

U.S. PATENT DOCUMENTS 5,741,645  4/1998  Orr et al. ...................................... 435/6
5,840,491  11/1998  Kakizuka ...................................... 435/6

OTHER PUBLICATIONS

Kawai, et al., *Analytical Biochemistry*, 209: 63–69 (1993).
Kawai, et al., *Human Immunology*, 41: 121–126 (1994).
Kawaguchi, *Nature Genetics*, 8: 221–226 (Nov., 1994).
Kawai, et al., *European Journal of Immunogenetics*, 23: 471–486 (1996).
Nance, *Brain Pathology*, 7: 881–900 (1997).

*Primary Examiner*—Stephanie W. Zitomer
*Assistant Examiner*—C. Wilder
*Attorney, Agent, or Firm*—Kenyon & Kenyon

[57] ABSTRACT

The invention provides a diagnostic method and kits for SCA III syndrome. The method comprises attaching a portion of SCA III gene containing copies of 73 trinucleotide (CAG) repeat units to a substrate; amplifying a DNA segment containing copies of the trinucleotide repeat units from the genomic DNA of a testee using two labeled primers under the suitable condition for carrying out polymerase chain reaction (PCR); hybridizing the gene with the PCR product by amplifying DNA segment; and analyzing the results of the hybridization. A SCA III patient can be effectively diagnosed by examining the increase extent of the number of the TNR characteristic of the disease-associated gene with the aid of reverse dot hybridization technique or PCR-MPH. Useful for the diagnosis is a kit which comprises the substrate, two primers with a detectable label, which are used to amplify a DNA segment containing copies of the trinucleotide repeat unit from the genomic DNA of a testee, a buffer and a polymerase for polymerase chain reaction, a buffer for gene hybridization and an enzyme for color detection.

8 Claims, 3 Drawing Sheets pSCAIII8   pSCAIII22   pSCAIII73 pSCAIII8   pSCAIII22   pSCAIII73

DIAGNOSTIC METHOD AND KIT FOR NEUROPSYCHIATRIC DISEASES USING TRINUCLEOTIDE REPEATS SEQUENCE

BACKGROUND OF THE INVENTION

The present invention relates to a diagnostic method and kits for neuropsychiatric diseases using trinucleotide repeats sequences. More particularly, the present invention relates to using gene amplification methodology and reverse dot-blot and oligonucleotide probe technology. The methods and probes of the invention specifically relate to the detection of the SCA III genes. The invention relates to the fields of molecular biology, diagnostic medicine.

Because of their unclear causes and nosagenic mechanisms, neuropsychiatric diseases are very difficult to diagnose and treat. In recent, some neuropsychiatric diseases have been found to be associated with characteristic genes. Accordingly, extensive research has been made to take advantage of the genes in diagnosing the diseases accurately.

Trinucleotide repeats (TNR) sequences are microsatellite DNA which occur as tandem repeats of a 3-bp sequence in the genome. These microsatellites are of special interest in human genetics, because they vary in length among individuals, making them highly useful for gene mapping as well as for clinical diagnosis or prognosis of some genetic diseases, especially neuropsychosis. For example, normal individuals have tens of copies of TNR in their genomic DNA. For patients suffering from neuropsychosis, the number of certain TNR was reported to be increased several to hundreds times as many as that of normal individuals.

In 1991, it was first reported that the number of the repeat (CGG)n are increased in the genome of fragile X syndrome patients. Since then, many reports have been published of such diseases associated with trinucleotide expansion, inclusive of Friedreich's ataxia in 1996, SCA VI syndrome and SCA VII syndrome in 1997. As many as 13 diseases are now found to be associated with trinucleotide repeat expansion.

A study of fragile X syndrome in which the chromosome Xq 27.3 (FRAXA) locus of the patients was cloned, revealed that the increased number of FRAXA is a common phenomenon to the patients (Yu, S. et al., Science, 252:1179–1181, 1991). In addition, such an expansion of a trinucleotide repeat is found in individuals affected with myotonic dystrophy, causing an instable mitosis which leads to somatic mosaicism.

Besides, examples of the diseases associated with the expansion of TNR include Huntington's disease, spinocerebellar ataxia type I (SCA I), X-linked spinobular atrophy (SBMA), dentatorubral and pallidoluysian atrophy (DRPLA), spinocerebellar ataxia type III (SCA III) and FRAXE mental retardation.

Recently molecular genetics have provided good evidence that some genetic neuropsychosis is primarily attributed to an increase in the number of TNR. The genes comprising TNR are thought to be expressed as kinases which play essential roles in the brain, but the correlation of TNR and nosagenic mechanism has not been clearly unveiled yet.

The diseases attributed to the TNR expansion show relatively common clinical options. In detail, there are four common clinical traits in such diseases: phenomenon of anticipation, inheritance disposition (autosomal dominant and sex chromosomal dominant), neural regression or mental retardation, and somatic mosaicism.

The phenomenon of anticipation is the pattern in which genetic diseases seem to display an earlier age of onset and more severe expression in more recent generations of a pedigree. That is, the degree of severity increases in each generation. For example, myotonic dystrophy is expressed differently in each generation of a three-generation family. Grandfather expresses the disease in the sixties or seventies, father in the thirties or forties, and grandson in the teens. DNA sequence analysis showed that a CGG repeat unit is present in 50 or less copies in normal individuals. Those with fragile X syndrome have 200 or more CGG repeats. An intermediate number of repeats, ranging approximately from 60 to 200, is seen in normal transmitting individuals, who carry the gene but do not express the disease, that is, who are of normal intelligence with no observation of the appearance characteristic of the patients. When the normal transmitting individuals transmit the gene to their offspring, there is often an expansion from 60–200 repeats to much more than 200 repeats. In addition to mental retardation, fragile X syndrome is characterized by an abnormal facial appearance with large ears, and macroorchidism in postpubertal males. This is observed in most of the diseases associated with TNR expansion, so that the prognosis of the diseases is possible.

As an example of the so-called dynamic mutation in genetics, autosomal dominant or sex chromosomal dominant inheritance is the phenomenon in which the genetic information which should remain as it is for continuous generations, is changed in just one next generation.

Neural regression or mental retardation is the very reason why the patients affected with the diseases go to hospital. As leading symtoms, metal retardation is shown in fragile X syndrome or FRAXA syndrome, muscular strength reduction resulting from progressive muscle deterioration in mytonic dystrophy, and ataxia in other diseases. Hence, the neuropsychiatric diseases can be diagnosed by investigating the genes of the patients who show the symptoms.

Somatic mosaicism, a characteristic trait of neuropsychosis, is detected by southern hybridization and methylation analysis with the gene of, for example, a fragile X syndrome patient or his family, whose result is a smeared band pattern in addition to a normal single band, showing that the increasing behavior of the number of the CGG repeat unit is different from generation to generation. This is attributed to the fact that the number of a CGG repeat unit is differently increased upon mitosis as well as meiosis. Also, a patient with fragile X syndrome was reported to have different numbers of the CGG repeat unit from organ to organ. This makes it difficult to accurately diagnose fragile X syndrome before birth through chorionic villous sampling. In fact, it was reported that methylation abnormality is not detected by the pre-parturient diagnosis while being evident in a peripheral blood test.

The neuropsychiatric diseases caused by an increase in the number of TNR have a common phenomenon that the sequence is repeated at the same gene locus of almost all patients. The gene mutation which is a cause for neuropsychiatric diseases seems to originate from the same ancestor (founder effect) because it is attributable to abnormality in a specific gene locus. In contrast, the mutation which causes Marfan syndrome or hereditary hypertrophic cardiomyopathy depending on autosomal dominent disease is relatively widely spread on many exons. Very exceptionally, there was found a fragile X syndrome which was caused by a mutation in an exon rather than by the TNRsequence. However, almost all neuropsychiatric diseases are caused by the mutation collected in one locus.

Linkage analysis demonstrated that the gene causing the neuropsychosis contains an increased number of TNR to give the same polymorphic marker on the chromosome.

By taking advantage of the fact that the neuropsychiatric diseases are caused by the simple mechanism of an increase in the number of TNR on a certain gene, they can be clinically diagnosed. That is, the diseases can be detected at high accuracy by investigating the increased degree of the number of TNR rather than all exonal mutations. Conventionally, fragile X syndrome was judged with an accuracy of 50% by investigating the X chromosomes from the cells of suspicious individuals, which are cultured in a medium deficient in folic acid.

Searching methods of the TNR associated the neuropsychosis were already developed and patented (U.S. Pat. Nos. 5,545,539, 5,650,277, 5,597,694, 5,723,301 and 5,582,979, and WO 97/27328). Particularly, the gene associated with Huntington's disease itself is patented (General Hospital Corporation; U.S. Pat. Nos. 5,538,844, 5,686,288 and 5,693, 757 and EP No. 0 814 977). However, nowhere has been reported methods for diagnosing neuropsychiatric diseases through the reverse dot hybridization or polymerase chain reaction-microplate hybridization (PCR-MPH) using gene loci containing TNR.

Application of these molecular genetic methods for neuropsychiatric diseases will guarantee highly accurate diagnosis. Particularly, reverse dot hybridization, a modified dot hybridization method in which after a probe is immobilized on a membrane or a plate, target DNA is hybridized with the probe and the hybrid is quantitated, is anticipated to be useful as a routine screening assay in hospitals, by virtue of the employment of many probes on one plate or membrane and a simple procedure.

An HLA typing method using PCR and reverse dot hybridization was developed and patent was filed (Japanese Pat. Appl'n No. Heisei 8-83480) by Wakunaga company of Japan. However, use of such a method in the diagnosis of neuropsychosis has not been reported at all.

SUMMARY OF THE INVENTION

Thorough and intensive research repeated by the inventors aims to developing effective diagnosis for neuropsychiatric diseases, resulted in the finding that a plasmid vector containing a neuropsychiatric disease-associated gene containing copies of a trinucleotide repeat unit can be utilized in accurately and simply diagnosing a neuropsychiatric disease through reverse dot hybridization or polymerase chain reaction-microplate hybridization.

Accordingly, it is an object of the present invention to overcome the problems encountered in prior arts and to provide a diagnosic method for genetic neuropsychiatric diseases, which is useful as a routine screening assay with high accuracy in hospitals.

It is another object of the present invention to provide a diagnostic kit for genetic neuropsychiatric diseases, with which the affection with and the severity of diseases can be accurately diagnosed.

In accordance with an aspect of the present invention, there is provided a diagnostic method for SCA III syndrome, comprising the steps of: attaching a portion of SCA III gene containing copies of 73 trinucleotide(CAG) repeat units to a substrate; amplifying a DNA segment containing copies of the trinucleotide repeat units from the genomic DNA of a testee using two labeled primers under the suitable condition for carrying out polymerase chain reaction (PCR); hybridizing the gene with the PCR product by amplifying DNA segment; and analyzing the results of the hybridization.

In accordance with another aspect of the present invention, there is provided a diagnostic kit for SCA III syndrome, comprising: a substrate to which a portion of SCA III gene containing copies of 73 trinucleotide(CAG) repeat units is attached; two primers with a detectable lable, which are used to amplify a DNA segment containing copies of the trinucleotide repeat unit from the genomic DNA of a testee; a buffer and a polymerase for polymerase chain reaction; a buffer for gene hybridization; and an enzyme for color detection.

In the kit according to the present invention, the neuropsychiatric disease-associated gene is a portion or the whole portion of TNR-containing gene in a form of a plasmid vector, an oligonucleotide or a DNA segment, the substrate comprises a membrane or a microplate, and the detectable label comprises 32P radiolabel or biotin-label.

The kit may further comprises a washing buffer, and an avidin-linked enzyme and a chromogenic substrate. Preferably, the avidin-linked enzyme is streptavidin-alkaline phosphatase.

In detail, SCA III gene is utilize as TNR-containing gene and SEQ ID NO: 1 [5'-CCAGTGACTACTTTGATTCG-3'] and SEQ ID NO: 2 [5'-TGGCCTTTCA CATGGATGTGAA-3'] oligonucleotides are used as the above primers.

In accordance with a further aspect of the present invention, there is provided a plasmid vector, pSCA III 73, under the Deposition No. KCTC 0435BP (deposited Feb. 9, 1998 with Korea Research Institute of Bioscience and Biotechnology, Korean Collection for Type Cultures, located #52, Oun-dong, Yuson-ku, Taejon 305–333, Republic of Korea), which contains a portion of an SCA III gene prepared from the genome of an SCA III syndrome patient.

In accordance with still another aspect of the present invention, there is provided a plasmid vector, pSCA III 8, which contains a portion of an SCA III gene prepared from the genome of a normal individual.

A: using the PCR product of normal individual

B: using the PCR product of SCA III patient

Figure 3:
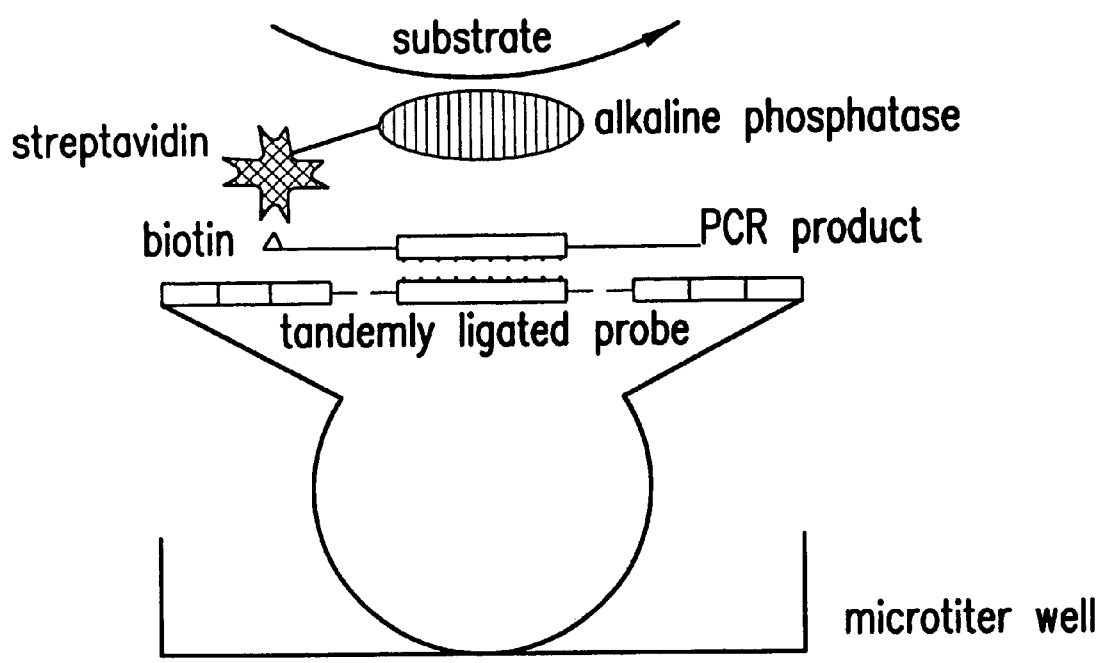

FIG. 3 shows the principle of MPH of the present invention.

DETAILED DESCRIPTION OF THE INVENTION

The present invention pertains to use of TNR in the diagnosis of genetic neuropsychiatric diseases. For this, reverse dot hybridization and PCR-MPH techniques are employed.

While dot blot hybridization is a technique in which a PCR product is blotted on a membrane, followed by the hybridization with a probe, plasmid probes are blotted on a membrane, followed by the hybridization with a labeled PCR product in reverse dot hybridization.

With an example of SCA III, a detailed description will be given of a novel diagnostic method and kit, below.

SCA III syndrome is a neuropsychiatric disease caused by an increased number of a trinucleotide CAG repeat unit in the polyglutamine tract gene. Normal individuals have 13–34 copies of the repeat unit in the chromosomes while it is present in 68–79 copies in the patients.

Figure 1:
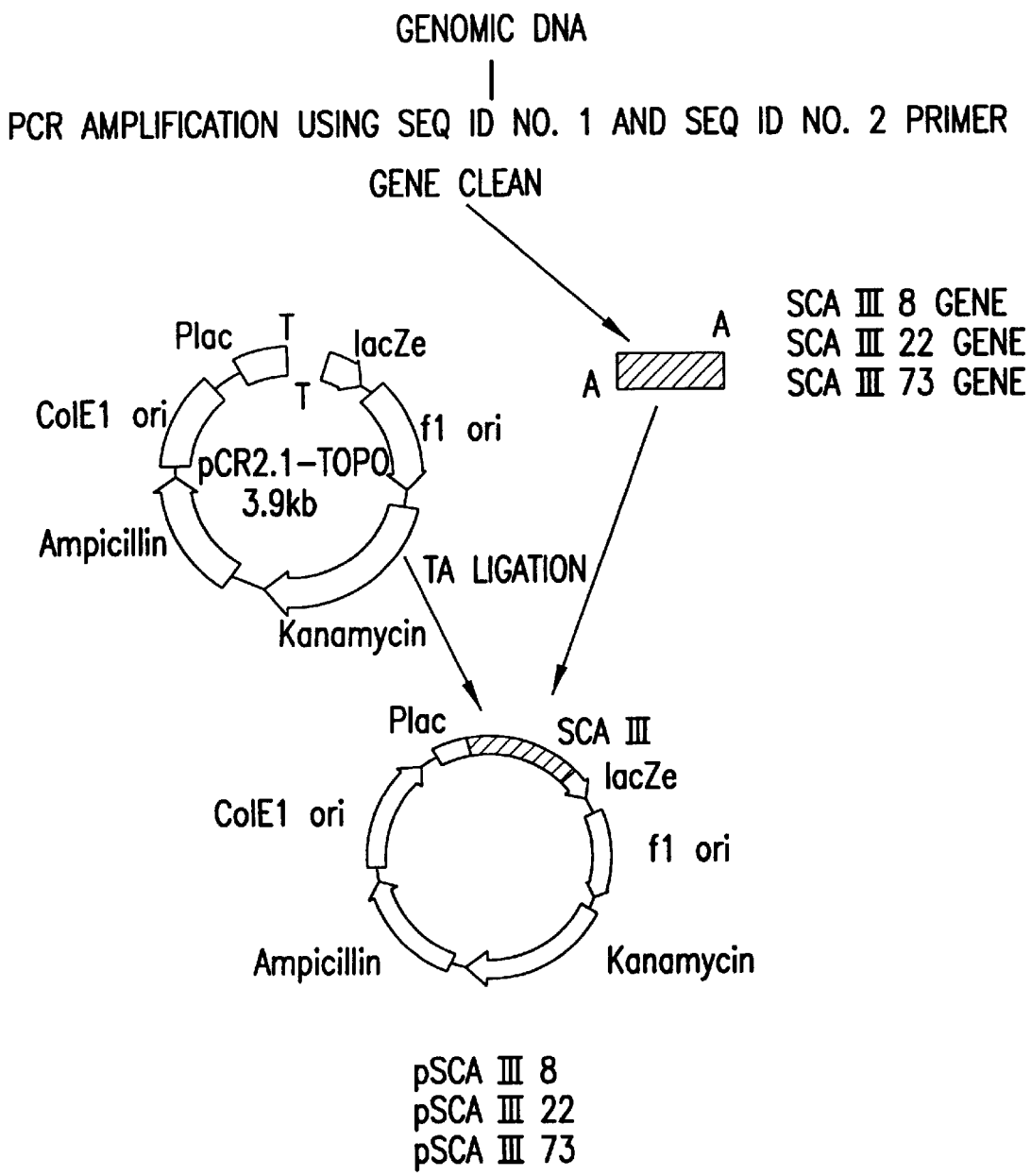
FIG. 1 shows a flow chart for the construction of vectors pSCA III 8, pSCA III 22 and pSCA III 73.

First, the increased number of TNR is examined with the SCA III gene located on chromosome 14q24.3 locus of an SCA III syndrome-suspected individual. After, amplified by PCR, a portion of the SCA III gene is inserted in a plasmid vector, as shown in FIG. 1. An SCA III gene of a patient affected with SCA III syndrome is cloned in the EcoRI restriction site of a plasmid vector pCR II 2.1-TOPO sold by Promega.

The resulting vector was named pSCA III 73 and deposited on Jan. 23, 1998 in Genetic Resources Center, the Korean Collection for Type Cultures of Korean Research Institute of Bioscience and Biotechnology under Budapest Treaty (Deposition No. KCTC 0435 BP). Likely, the SCA III gene of a normal individual is inserted in a plasmid vector pCR II 2.1-TOPO, to give vectors pSCA III 22 and pSCA III 8. Thus, all of the plasmids in which the TNR-containing SCA III genes of normal and affected individuals are inserted partially or wholly, is within the scope of the present invention.

In accordance with the present invention, the neuropsychiatric diseases associated with TNR expansion can be diagnosed by a reverse dot hybridization technique. For this, the TNR-containing plasmid prepared is transferred on a nylon membrane and then, hybridized with the PCR product which has been obtained by using as a template the DNA isolated from the patient to be diagnosed, with the primers having a detectable marker. The hybrids are analyzed by autoradiography, coloring assay, etc.

As for the primers for PCR, they are two synthetic oligonucleotides complementary to the 3' ends of the double-strand DNA segment of interest and labeled with a radioactive isotope or biotin. In accordance with the present invention, the SCA III gene segment containing TNR of the patient to be diagnosed, is amplified by using as primers SEQ ID NO: 1 and SEQ ID NO: 2. The hybridization is carried out in a buffer comprising 6× SSC, 5× Denhart solution 0.1% salmon sperm DNA.

Figure 2A:
FIG. 2 shows the reverse dot hybridization results using vectors pSCA III 8, pSCA III 22 and pSCA III 73 to the patient and normal individual.
Figure 2B:
Figure 2B:

Intensive signals were detected by use of the plasmid vector pSCA III 22 and pSCA III 8 for normal individuals and the plasmid vector pSCA III 73 for neuropsychosis-ill individuals as measured by autoradiography or coloring assay (FIG. 2). Thus, this can be used to diagnose the affection of a person with neuropsychosis and the severity of the disease.

The PCR template may be obtained from the blood of the individual to be diagnosed. Genomic DNA is isolated from the blood and subjected to PCR to amplify the segment of interest. This DNA segment is added in the membrane or well plate which immobilizes pSCA III 8 and pSCA III 73. If an intensive signal is detected from the plasmid pSCA III 8, the individual is normal. On the other hand, if an intensive signal is detected from the plasmid pSCA III 73, he or she is a patient.

In the case of PCR-MPH, the probe containing copies of TNR is first immobilizd on the wells of a microplate. Together with the primers which are biotin-labeled, a DNA segment of interest which contains copied of the TNR is subjected to a PCR apparatus. An amplified DNA segment is hybridized with the immobilized probe. Following hybridization, the microplate is washed with a buffer and added with streptavidin-alkaline phosphatase and chromogenic substrate. Various degrees of the color resulting from the action of the enzyme can be quantitated by measuring the absorbance at 450 nm.

As the probe, it comprises DNA segments correlated with neuropsychiatric diseases, and ssDNA-containing tandemly ligated probes which have the above DNA segment. In order to be used as primers in the PCR-MPH, oligonucleotides having the base sequences of SEQ ID NO: 1 and SEQ ID NO: 2 are labeled with $^{32}P$ or biotin at their 5' ends.

As mentioned above, the reverse dot hybridization and PCR-MPH according to the present invention can be used to diagnose all genetic neuropsychiatric diseases by employing various primers and probes, A better understanding of the present invention may be obtained in light of the following examples which are set forth to illustrate, but are not to be construed to limit the present invention.

COMPARATIVE EXAMPLE I

Southern Hybridization

In this example, a conventional southern hybridization technique was used to diagnose a neuropsychiatric disease.

Total DNA was isolated from the peripheral blood taken from each members of a family who suffered from a neuropsychiatric disease. The total DNA thus obtained was digested with EcoRI and electrophoresed on a 0.7% agarose gel. The seperated DNA segments were transferred on a nylon membrane, such as that sold by Amersham under the tradename of Hybond N, by blotting, after which a hybridization process was carried out at 65° C. in a buffer containing 6× SSC, 5× Denhart solution and 0.1% salmon sperm DNA. As a probe for the hybridization, a plasmid vector containing the 3'-end region of the SCA III gene was labeled with $[\alpha-^{32}P]dATP$ by a random priming method. The hybridization cotinued to proceed for 12–18 hours. After being washed with a buffer, the membrane was subjected to autoradiography.

EXAMPLE I

Reverse Dot Hybridization

Total DNA was isolated from the peripheral blood taken from an individual who was proved to be an SCA III patient. Using this total DNA as a template, a polymerase chain reaction (PCR) was carried out to amplify the SCA III DNA region, after which the PCR product (SEQ ID NO: 3)

| | |
|---|---:|
| 5'-CCA GTG ACT ACT TTG ATT CGT GAA ACA ATG TAT TTT CCT TAT GAA | 45 |
| TAG TTT TTC TCA TGG TGT ATT TAT TCT TTT AAG TTT TGT TTT TTA | 90 |
| AAT ATA CTT CAC TTT TGA ATG TTT CAG ACA GCA GCA AAA GCA GCA | 135 |
| A CAG CAG CAG CAG CAG CAG CAG CAG CAG CAG CAG CAG CAG CAG CAG | 181 |
| CAG CAG CAG CAG CAG CAG CAG CAG CAG CAG CAG CAG CAG CAG CAG | 226 |
| CAG CAG CAG CAG CAG CAG CAG CAG CAG CAG CAG CAG CAG CAG CAG | 271 |
| CAG CAG CAG CAG CAG CAG CAG CAG CAG CAG CAG CAG CAG CAG CAG | 316 |
| CAG CAG CAG CAG CAG CAG CAG CAG CAG CAG CAG CAG CAG CGG GAC | 361 |
| CTA TCA GGA CAG AGT TCA CAT CCA TGT GAA AGG CCA-3' | 397 | was inserted in a plasmid vector: the SCA III PCR product was digested with EcoRI and inserted in a plasmid pCR II 2.1-TOPO which was opened at the EcoRI restriction site to give a novel vector, named pSCA III 73. For a normal individual, the same procedure as in the patient was repeated. As a result, two recombinant plasmid, named pSCA III 22 and pSCA III 8, were obtained.

Each of the plasmids was transferred on a nylon membrane, such as that sold by Amersham under the tradename of Hybond N+, by a blotting method (Sambrook et al., Molecular Cloning). A PCR in which the DNA from testees and $^{32}$P radiolabeled or biotin-labeled oligonucleotides having the base sequences of SEQ ID NO: 1 and SEQ ID NO: 2 were used as a template and primers, respectively, was carried out in the manner of the following Example II, to amplify the SCA III DNA region. Thereafter, the PCR products were hybridized with the blotted plasmids in the same manner as in Comparative Example I, followed by subjecting the hybrids to autoradiography and coloring analysis.

For normal individuals, an intensive signal was detected from the blotted membranes of the plasmids pSCA III 22 and pSCA III 8, while an intensive signal from the blotted membrane of the plasmid pSCA III 73 for patients. Accordingly, a diagnosis for the affection with and the severity of the disease could be made.

EXAMPLE II

Polymerase Chain Reaction

Genetic DNA was isolated from the peripheral blood of a neuropsychiatric patient and used as a template in a PCR to amplify the TNR sequence of the SCA III gene. As the primers for this PCR, two oligonucleotides were constructed to have the base sequences of 5'-CCAGTGACTACTTTGATTCG-3' (SEQ ID NO: 1, MJD52) and 5'-TGGCCTTTCACATGGATGTGAA-3' (SEQ ID NO: 2, MJD25), respectively. These primers have already disclosed in *Nature Genetics* Vol. 8, pp 221–228 (1994).

A mixture of genomic DNA φng, SEQ ID NO: 1 primer and SEQ ID NO: 2 primer each 0.5 μM, dATP, dGTP and dTTP each 200 μM, dCTP 50 μM, and 0.3 μCi[α-$^{32}$P]-dCTP was added with 1× PCR buffer solution (50 mM potassium chloride, 10 mM Tris-HCl pH 8.3, 1.5 mM magnesium chloride) to make a final volume of 20 μl. This PCR mixture was denaturated at 95° C. for 5 min, followed by adding Taq polymerase at an amount of 2U to the mixture for hot starting. The PCR consisted of 30 thermal cycles in each of which a denaturing process at 95° C. for 1 min, an annealing process at 55° C. for 1 min and an extension process at 72° C. for 1 min occurred.

A portion of the PCR product thus obtained was electrophoresed on a sequencing gel (6% polyacrylamide/8M urea) to determine the base sequence.

EXAMPLE III

PCR-MPH Using TNR

An ssDNA-containing tandemly ligated probe which had the TNR, was immobilized on a microplate. In the wells of the microplate was added the genomic DNA of a testee. A PCR was performed using as primers the Sequences I and II whose 5'-ends were labeled with biotin, in the microplate wells to amplify the SCA III gene region. The PCR products thus obtained were subjected to hybridization. Subsequently, the wells were washed with TMAC buffer (3M tetraammonium chloride, 500 mM Tris-HCl pH 7.5, 2 mM EDTA). To the PCR product attached to the wells, a chromogenic substrate and a streptavidin-alkaline phosphatase were added and reacted. The absorbance at 450 nm of the wells was read by a microtiter plate reader (FIG. 3).

As described hereinbefore, the SCA III syndrome, a neuropsychiatric disorder, can be effectively diagnosed by examining the increase extent of the number of the TNR characteristic of the SCA III gene with the aid of reverse dot hybridization technique or PCR-MPH. This molecular genetic analysis for the number of TNR provides 99% or more diagnosis accuracy for genetic neuropsychiatric diseases, which is higher than that given by any other methods. Moreover, from the fact that normal transmitting individuals, who carry the problematic genes but do not express the disease, have somewhat more copies of TNR than do mormal individuals and that the more the number of TNR, the severer is the disease, the prognosis for neuropsychosis can be made, which is helpful in treating the patients. Therefore, the method according to the present invention allows the clinical diagnosis of neuropsychiatric patients as well as prognosis for whether the family members are affected with the disease. In addition, the method can give an anticipation for when and to what degree of severity the diseases are expressed, so it is very useful as a general screening assay for the diagnosis and treatment of neuropsychiatric diseases.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A diagnostic method for detecting spinocerebellar ataxia type III ("SCA III III") syndrome, comprising the steps of:

attaching a portion (SEQ ID NO: 3) of a spinocerebellar ataxia type III ("SCA III") gene containing copies of 73 trinucleotide (CAG) repeat units to a substrate;

amplifying a DNA segment containing copies of the trinucleotide repeat units from the genomic DNA of a testee using two labeled primers (SEQ ID NO: 1 and SEQ ID. NO: 2) using a polymerase chain reaction (PCR) to produce a PCR product;

hybridizing the SCA III gene with the PCR product; and analyzing the results of the hybridization.

2. A diagnostic kit for detecting SCA III syndrome in a patient, comprising: a substrate to which a portion (SEQ ID NO: 3) of a SCA III gene said portion containing copies of 73 trinucleotide (CAG) repeat units is attached;

two primers (SEQ ID NO: 1 and SEQ ID. NO: 2) labeled with a detectable label, a buffer and a polymerase for polymerase chain reaction;

a buffer for gene hybridization; and an enzyme for color detection.

3. The diagnostic kit as set forth in claim 2, wherein said SCA III gene is in a form of a plasmid vector, an oligonucleotide or a DNA segment.

4. The diagnostic kit as set forth in claim 2, wherein said substrate comprises a membrane or a microplate.

5. The diagnostic kit as set forth in claim 2, wherein said detectable label comprises $^{32}P$ radiolabel or biotin-label.

6. The diagnostic kit as set forth in claim 5, further comprising:

a washing buffer, and an avidin-linked enzyme and a chromogenic substrate.

7. A plasmid vector, pSCA III 73, under the Deposition No: KCTC 0435BP, which contains a portion of an SCA III gene (SEQ ID NO: 3) prepared from the genome of an SCA III syndrome patient.

8. A plasmid vector, pSCA III 8, which contains a portion of an SCA III gene prepared from the genome of a normal individual.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: human

<400> SEQUENCE: 1
ccagtgacta ctttgattcg                                           20

<210> SEQ ID NO 2
<211> LENGTH: 22
<212> TYPE: DNA

-continued

```
<213> ORGANISM: human

<400> SEQUENCE: 2
tggcctttca catggatgtg aa                                              22

<210> SEQ ID NO 3
<211> LENGTH: 397
<212> TYPE: DNA
<213> ORGANISM: human

<400> SEQUENCE: 3
ccagtgacta ctttgattcg tgaaacaatg tattttcctt atgaatagtt tttctcatgg     60
tgtatttatt cttttaagtt ttgttttta aatatacttc acttttgaat gtttcagaca     120
gcagcaaaag cagcaacagc agcagcagca gcagcagcag cagcagcagc agcagcagca    180
gcagcagcag cagcagcagc agcagcagca gcagcagcag cagcagcagc agcagcagca    240
gcagcagcag cagcagcagc agcagcagca gcagcagcag cagcagcagc agcagcagca    300
gcagcagcag cagcagcagc agcagcagca gcagcagcag cagcagcagc agcagcggga    360
cctatcagca cagagttcac atccatgtga aaggcca                             397
```